US012049650B2

(12) United States Patent
Vihinen et al.

(10) Patent No.: US 12,049,650 B2
(45) Date of Patent: Jul. 30, 2024

(54) DESTABILISING DOMAINS FOR CONDITIONALLY STABILISING A PROTEIN

(71) Applicant: BrainGene AB, Lund (SE)

(72) Inventors: Mauno Vihinen, Lund (SE); Deniz Kirik, Lund (SE)

(73) Assignee: BRAINGENE AB, Lund (SE)

( * ) Notice: Subject to any disclaimer, the term of this patent is extended or adjusted under 35 U.S.C. 154(b) by 0 days.

(21) Appl. No.: 17/674,220

(22) Filed: Feb. 17, 2022

(65) Prior Publication Data

US 2022/0169993 A1 Jun. 2, 2022

Related U.S. Application Data

(63) Continuation of application No. 16/302,897, filed as application No. PCT/EP2017/062150 on May 19, 2017, now abandoned.

(30) Foreign Application Priority Data

May 20, 2016 (SE) .................................... 1650693-3

(51) Int. Cl.
*C12N 9/06* (2006.01)
*A61K 38/00* (2006.01)
*C12N 15/62* (2006.01)

(52) U.S. Cl.
CPC ............. *C12N 9/003* (2013.01); *C12N 15/62* (2013.01); *C12Y 105/01003* (2013.01); *A61K 38/00* (2013.01); *C07K 2319/02* (2013.01); *C07K 2319/35* (2013.01)

(58) Field of Classification Search
CPC ................... C12N 9/003; C12N 15/62; C12Y 105/01003; A61K 38/00; C07K 2319/02; C07K 2319/35
See application file for complete search history.

(56) References Cited

U.S. PATENT DOCUMENTS

| | | | |
|---|---|---|---|
| 4,868,116 | A | 9/1989 | Morgan et al. |
| 5,399,346 | A | 3/1995 | Anderson et al. |
| 5,677,158 | A | 10/1997 | Zhou et al. |
| 6,309,634 | B1 | 10/2001 | Bankiewicz et al. |
| 6,451,306 | B1 | 9/2002 | Tuszynski et al. |
| 6,683,058 | B1 | 1/2004 | Tuszynski |
| 2002/0037281 | A1 | 3/2002 | Davidson et al. |
| 2009/0215169 | A1 | 8/2009 | Wandless et al. |
| 2014/0010791 | A1 | 1/2014 | Wandless et al. |
| 2017/0369870 | A1 | 12/2017 | Gill et al. |

FOREIGN PATENT DOCUMENTS

| | | | |
|---|---|---|---|
| WO | 9524929 | A2 | 9/1995 |
| WO | 9530761 | A2 | 11/1995 |
| WO | 2015152813 | A1 | 10/2015 |

OTHER PUBLICATIONS

Singh RK et al. Protein Engineering Approaches in the Post-Genomic Era. 2017. Current Protein and Peptide Science. 18, 1-11. (Year: 2017).*
Zhang M et al. Propagated Perturbations from a Peripheral Mutation Show Interactions Supporting WW Domain Thermostability. 2018. Structure. 26, 1474-1485. (Year: 2018).*
Bachmair et al.; Science, vol. 234; 1986; pp. 179-186.
Banerji et al.; Cell, 1981; vol. 27; pp. 299-308.
Breathnach et al.; Ann. Rev. Biochem, 1981; vol. 50; pp. 349-383.
Capecchi et al.; Cold Spring Harbor Laboratories, 1991; pp. 101-102.
Corden et al.; Science, 1980; vol. 209; No. 4463; pp. 1406-1414.
De Wet et al.; J. Biol. Chem. 1983; vol. 258; No. 23; pp. 14385-14389.
Dohmen et al.; Science, 1994; vol. 263; No. 5151; pp. 1273-1276.
Fire et al.; Nature, 1998; vol. 391; pp. 806-811.
Gaffar et al.; Molecular & Biochemical Parasitology, 2004; vol. 133; pp. 209-219, fig. 2.
Iwamoto et al.; Chemistry & Biology; vol. 17; pp. 981-988; p. 982, col. 1. paragraph [0002]; p. 986, col. 2, paragraph [0003]; p. 987, col. 1, paragraph [0004].
Janse et al.; J. Biol. Chem., 2004; vol. 279: No. 20; pp. 21415-21420.
Jolly et al.; Nucleic Acids Res., 1983; vol. 11; No. 6; 1855-1872.
Kanemaki et al.; Nature, 2003; vol. 423; pp. 720-724.
Labib et al.; Science, 2003; vol. 288; pp. 1643-1646.
Matthews et al.; Methods in Enzymology, 1985; vol. 115; pp. 397-420.
Medema, Rene H.; Biochem. J., 2004; vol. 380; pp. 593-603.
Ohmae et al.; Journal of Biochemistry, 2001; vol. 130, No. 3; pp. 439-447.
Park et al.; Proc. Natl. Acad. Sci. U.S.A., 1992; vol. 89; pp. 1249-1252.
Prockop et al.; N. Eng. J. Med., 1984; vol. 311; No. 6; pp. 376-387.
Proudfoot et al.; The Journal of Biological Chemistry, 1989; vol. 264; No. 15; pp. 8764-8770.
Rossi et al.; Proc. Natl. Acad. Sci. USA, 1987; vol. 84; pp. 5590-5594.
Roth et al.; J Med Chem., 1987; vol. 30; No. 2; pp. 348-356.
Ryding et al.; J. Endocrinol., 2001; vol. 171; pp. 1-14.
Schmidt et al.; Nature, 1985; vol. 314; pp. 286-289.
Schneekloth et al.; J. Am. Chem. Soc., 2004; vol. 126; pp. 3748-3754.
Schnell et al.; Annu. Rev. Biophys. Biomol. Struct., 2004; vol. 33; pp. 119-140.
Schweitzer et al.; The FASEB Journal, 1990; vol. 4; pp. 2441-2542.
Smith et al.; Biochemistry, 1980; vol. 19; pp. 1820-1825.
(Continued)

*Primary Examiner* — Paul J Holland
(74) *Attorney, Agent, or Firm* — Dinsmore & Shohl LLP

(57) ABSTRACT

The present disclosure relates to mutant polypeptides derived from *Escherichia coli* dihydrofolate reductase (DHFR) which can be fused to a polypeptide of interest for efficient conditional modulation of its activity. Also disclosed are polynucleotides encoding such mutant polypeptides, vectors comprising such polynucleotides, and the use of such polypeptides, polynucleotides and vectors for treating a disorder.

22 Claims, 2 Drawing Sheets

Specification includes a Sequence Listing.

(56) References Cited

OTHER PUBLICATIONS

Takahashi et al.; Epidemiology of Antimicrobial Resistance, 2002; vol. 51, pp. 510-515; abstract, fig. 1.
Tian et al.; PLOS Computational Biology, 2015; pp. 1-27; Abstract, table S1.
Weiss et al.; Cold Spring Harbor Laboratory, 1982.
Yao Fan et al.; Biochemistry, 2013; vol. 52; No. 12; pp. 2036-2049.
Garst et al.; Nature Biotechnology; vol. 35, No. 1; pp. 48-55; Supplementary Figures; Year 2016.
Garst et al.; Nature Biotechnology; vol. 35, No. 1; pp. 48-55; doi:10.1038/nbt.3718; Year 2016.
Dion et al.; Biochemistry, vol. 32, No. 13; pp. 3479-3487. Year 1993.
Murphy DJ et al. Hydrophobic Interactions via Mutants of *Escherichia coli* Dihydrofolate Reductase: Separation of Binding and Catalysis. Biochemistry 1989, 28, 3025-3031 (Year: 1989).
Lo K et al. High level expression and secretion of Fc-X fusion proteins in mammalian cells. Protein Engineering vol. 11 No. 6 pp. 495-500, 1998 (Year: 1998).
Rajagopalan PTR et al. Interaction of dihydrofolate reductase with methotrexate: Ensemble and single-molecule kinetics. PNAS. Oct. 15, 2002. vol. 99, No. 21. pp. 13481-13486 (Year. 2002).
Siloto R et al. Site saturation mutagenesis: Methods and applications in protein engineering. Biocatalysis and Agricultural Biotechnology 1 (2012)181-189. (Year: 2012).
Arai and Iwakura, J.Mol. Biol., vol. 347, p. 33-353; Year 2005.
Database EMBLWGS [Online] EBI; Apr. 17, 2014 (Apr. 17, 2014), "*Escherichia coli* 1-110-08_S3_c3 dihydrofolate reductase", XP002797513, retreived from EBI accession No. EYE15755; Year 2014.
Database PATRIC [Online] Apr. 6, 2016 (Apr. 6, 2016), "Dihydrofolate reductase (EC 1.5.1.3), folA from Klebsiella pneumoniae strain PB497",XP002797514, accession No. figI573.5818.peg.5079 Database accession No. figI573.5818.peg.5079 I SAMEA3531858_03491; Year 2016.
Maniatus; Polyacrylamide Gel Electrophoresis; pp. 173-177; Published prior to Mar. 7, 2019.
Bershtein, S., et al., Protein quality control acts on folding intermediates to shape the effects of mutations on organismal fitness, Molecular Cell, 49(1): 133-144, Jan. 10, 2013.
Singh, P., et al., Extension and limits of the network of coupled motions correlated to hydride transfer in dihydrofolate reductase, Journal of the American Cancer Society, 136(6): 2575-82, Feb. 12, 2014.

* cited by examiner

SEQUENCE LISTING

```
<160> NUMBER OF SEQ ID NOS: 3

<210> SEQ ID NO 1
<211> LENGTH: 159
<212> TYPE: PRT
<213> ORGANISM: Escherichia coli

<400> SEQUENCE: 1

Met Ile Ser Leu Ile Ala Ala Leu Ala Val Asp Arg Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Gly Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155


<210> SEQ ID NO 2
<211> LENGTH: 159
<212> TYPE: PRT
<213> ORGANISM: Escherichia coli

<400> SEQUENCE: 2

Met Ile Ser Leu Ile Ala Ala Leu Ala Val Asp Tyr Val Ile Gly Met
1               5                   10                  15
```

-continued

```
Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155


<210> SEQ ID NO 3
<211> LENGTH: 15
<212> TYPE: PRT
<213> ORGANISM: Artificial sequence
<220> FEATURE:
<223> OTHER INFORMATION: Examplary linker

<400> SEQUENCE: 3

Gly Gly Gly Gly Ser Gly Gly Gly Gly Ser Gly Gly Gly Gly Ser
1               5                   10                  15
```

DESTABILISING DOMAINS FOR CONDITIONALLY STABILISING A PROTEIN

CROSS REFERENCE TO RELATED APPLICATIONS

This application is a continuation of U.S. patent application Ser. No. 16/302,897 filed Nov. 19, 2018, which is a U.S. National Stage under 35 U.S.C. § 371 of PCT/EP2017/062150 filed May 19, 2017, which depends from and claims priority to Sweden Application No: 1650693-3 filed May 20, 2016, the entire contents of each of which are incorporated herein by reference.

SEQUENCE LISTING

The instant application contains a Sequence Listing that has been submitted in ASCII format via EFS-Web and is hereby incorporated by reference in its entirety. Said ASCII copy, created on Feb. 17, 2022, is named 2022-02-17_Sequence_Listing_16 VIKI-H068603NA.txt and is 3,335 bytes in size.

FIELD OF INVENTION

The present invention provides mutant polypeptides derived from *Escherichia coli* dihydrofolate reductase (DHFR) which can be fused to a polypeptide of interest for efficient conditional modulation of its activity. Also disclosed are polynucleotides encoding such mutant polypeptides, vectors comprising such polynucleotides, and the use of such polypeptides, polynucleotides and vectors for treating a disorder.

BACKGROUND OF INVENTION

The rapidly changing field of gene therapy promises a number of innovative treatments for patients suffering from a variety of diseases. Advances in genetic modification of cancer and immune cells and the use of oncolytic viruses and bacteria have led to numerous clinical trials for cancer therapy, with several progressing to late-stage product development. Similarly, multiple clinical trials are underway testing the efficacy of viral vectors (especially those based on recombinant adeno-associated viruses) for treatment of the diseases of the nervous system and eye diseases. At the time of this writing, very few gene therapy products have been approved by the United States Food and Drug Administration (FDA) and the European Medicines Agency (EMA). Some of the key scientific and regulatory issues include understanding of gene transfer vector biology, safety of vectors in vitro and in animal models, optimum gene transfer, long-term persistence or integration in the host, shedding of a virus and ability to maintain transgene expression in vivo for a desired period of time.

Techniques that target gene function at the level of DNA and mRNA provide powerful methods for modulating the expression of proteins encoded by specific genes. For example, the Cre/lox and tet/dox systems have been widely used to target gene expression at the transcriptional level (Ryding et al., 2001) and RNA interference as a method to achieve post-transcriptional gene silencing (Fire et al., 1998; Madema, 2004). One of the major drawbacks of such methods in the context of gene therapy is that they often result in relatively high basal levels of transgene even when not induced.

Methods for regulating protein activity, where the protein encoded by the transgene is inactive or degraded in the absence of a specific ligand, are promising alternatives.

However, methods for regulating protein function directly are limited, especially in mammalian cells. Inhibitors or activators of particular proteins have been identified, and often take the form of cell-permeable small molecules. Many of these molecules have found widespread use as biological probes, often because of the speed, dosage-dependence, and reversibility of their activities, which complement methods for modulating gene expression at the DNA or RNA level. However these inhibitors or activators are often promiscuous, affecting several proteins rather than a specific protein.

Alternative strategies to perturb protein function by exploiting existing cellular processes have been devised. For example, Varshaysky and coworkers developed methods for controlling protein function based on the importance of certain N-terminal residues for protein stability (Bachmair et al., 1986). Szostak and coworkers showed that a small peptide sequence could be fused to the N-terminus of a protein of interest to modulate protein stability (Park et al., 1992). Varshaysky and coworkers have further isolated a temperature-sensitive peptide sequence that greatly reduced the half-life or dihydrofolate reductase (DHFR) at the non-permissive temperatures (Dohmen et al., 1994). This approach has been used to study proteins in yeast (Labib et al., 2000; Kanemaki et al., 2003). More recently, several researchers have engineered systems in which dimeric small molecules are used to conditionally target fusion proteins for degradation via E3 ligase or the proteasome, itself (Schneekloth et al., 2004; Janse et al., 2004). However, these systems require either a prior knowledge of the high-affinity ligands that modulate the activity of a protein of interest or they are restricted to genetically engineered yeast strains.

An alternative approach for controlling protein function directly is to interfere with subcellular localization. Several methods are available to regulate protein localization using small-molecules by taking advantage of the FKBP-rapamycin-FRB ternary complex.

U.S. application Ser. No. 12/069,235 describes mutant polypeptides derived from *Escherichia coli* dihydrofolate reductase (DHFR) for conditionally controlling expression of a protein to which the mutant polypeptides are fused. The resulting fusion protein is unstable and has reduced activity in the absence of e.g. trimethoprim (TMP), which is a DHFR inhibitor. In the presence of TMP, the fusion protein is stabilised and active.

In WO 2015/152813, this approach has been taken advantage of to develop a system for conditionally stabilising a therapeutic protein, namely GTP cyclohydrolase 1 (GCH1) by fusion to a destabilising domain of DHFR. The resulting fusion protein together with tyrosine hydrolase (TH) is used for gene therapy, where administration of a ligand such as TMP ensures that GCH1 is only fully active when the ligand is present.

There is however still a need for reliable, tunable and efficient methods for conditionally stabilising a protein of interest, where the basal activity level in the absence of ligand is even further reduced.

SUMMARY OF INVENTION

The present disclosure relates to mutant polypeptides derived from *Escherichia coli* dihydrofolate reductase (DHFR) which can be fused to a polypeptide of interest for efficient conditional modulation of its activity. Also disclosed are polynucleotides encoding such mutant polypeptides, vectors comprising such polynucleotides, and the use of such polypeptides, polynucleotides and vectors for treating a disorder.

In a first aspect, the present disclosure relates to a mutant polypeptide derived from DHFR comprising or consisting of a sequence differing from SEQ ID NO: 1 and SEQ ID NO: 2 in at least one of the following positions: W133, F153, R12, N18, M42, Y100, D122, P126 and/or D127, with the proviso that the mutant polypeptide does not differ from SEQ ID NO: 1 and SEQ ID NO: 2 only by a Y100I mutation.

The mutations at positions W133, F153 share the common feature that they result in a particularly high degree of destabilization, which can be fully recovered when TMP is applied as a ligand. This is evident from Table 2 in the examples. Table 2 shows a very high fluorescence from reporter protein YFP in the presence of TMP and a very low fluorescence when TMP is absent, i.e. when the protein is destabilized by the mutant DHFR.

In a further aspect, a fusion polypeptide comprising the mutant polypeptide as described herein linked to a polypeptide of interest is provided.

In yet a further aspect, is provided a polynucleotide encoding the mutant polypeptide or the fusion polypeptide as described herein.

In yet a further aspect, a gene expression system comprising a polynucleotide as disclosed herein is provided.

Also provided is a system for conditionally stabilising a fusion polypeptide comprising a polypeptide and a ligand as described herein, wherein the ligand is capable of binding to the polypeptide and stabilising the fusion polypeptide.

DEFINITIONS

Figure 1:
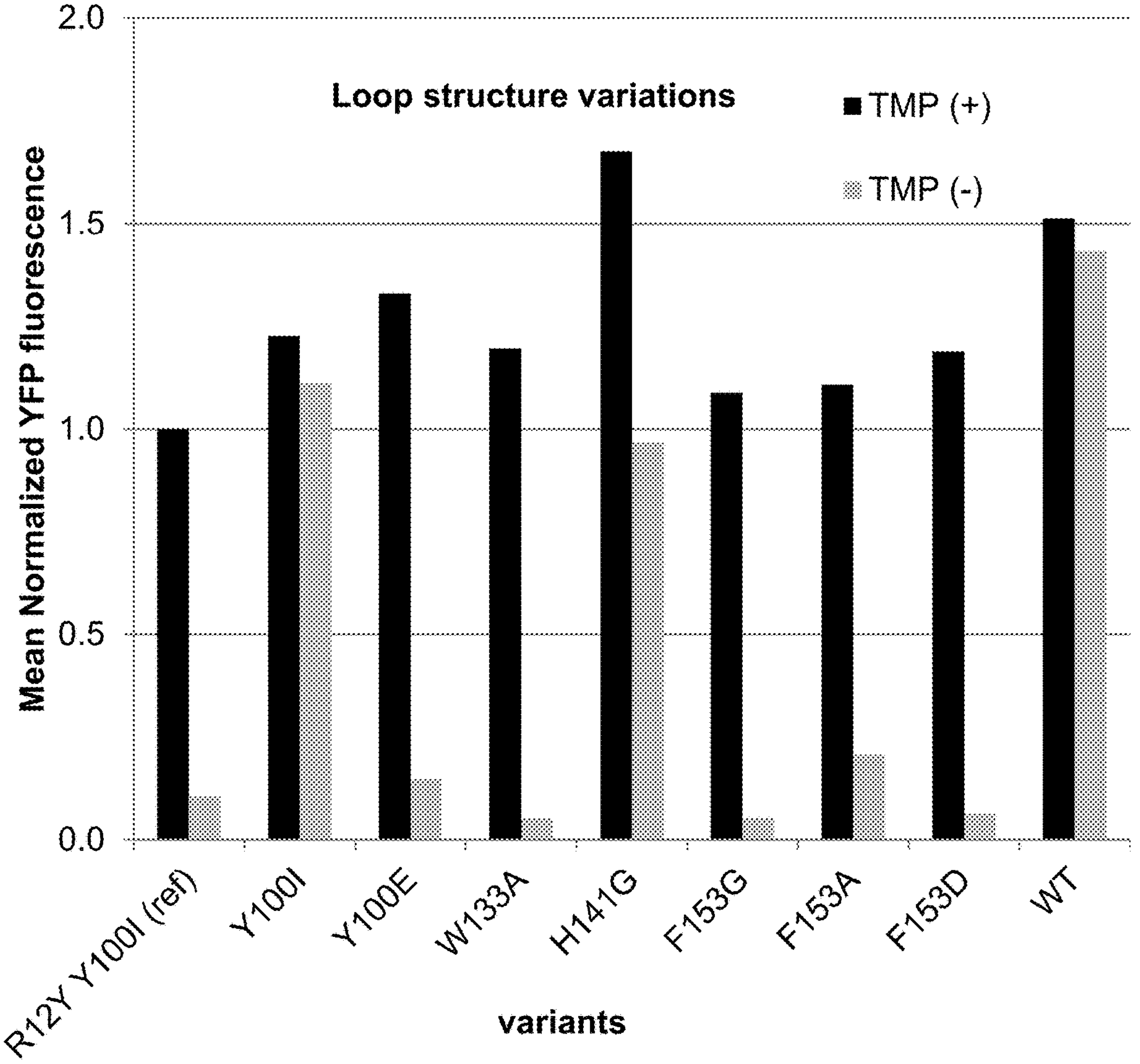
FIG. 1. Effect of loop structure variations on the reversible destabilization of the DHFR domain fused to YFP reporter protein. Variations on W133, H141, and F153 were studied in the presence (black bars) and absence (grey bars) of the TMP inhibitor and compared to reference construct containing the R12Y and Y100I variations (left most pair of bars). Note that the YFP fluorescence is not dependent on the presence of TMP when fused to the WT DHFR domain (right most pair of bars).

The term "system", as used herein, denotes a system specifically designed for production of a specific gene product, which in this case is a fusion protein, as specified in the claims and explained in further detail below. The gene expression system may be used in vitro, but in many embodiments it is intended to be used in gene therapy, both in vivo and ex vivo.

In the context of the present disclosure, the terms "polypeptide" and "protein" are used interchangeably. They both relate to a compound consisting of a contiguous sequence of amino acid residues linked by peptide bonds.

Furthermore, in the context of polypeptides discussed herein, the term "based on" may be used interchangeably with the term "derived from". A polypeptide or peptide, or fragment thereof, derived from a specific polypeptide or peptide ("parent polypeptide") has an amino acid sequence that is homologous to but not 100% identical with the parent polypeptide. A derivative is thus a polypeptide or peptide, or fragment thereof, derived from a parent polypeptide. An analogue is such a derivative that has essentially the same function or exactly the same function as the parent polypeptide.

In the context of polypeptides discussed herein, the term "variant" may be used interchangeably with the term "derived from". The variant may be a polypeptide having an amino acid sequence that does not occur in nature.

A mutant polypeptide or a mutated polypeptide is a polypeptide that has been designed or engineered in order to alter the properties of a parent polypeptide. A mutant polypeptide derived from DHFR and comprising or consisting of a sequence differing from a parent sequence in at least one position refers to a polypeptide having essentially the same sequence as the parent sequence except in the indicated positions. By way of example, a mutant polypeptide derived from DHFR and comprising or consisting of a sequence differing from SEQ ID NO: 1 at least in position R12 and having at least 70% identity to SEQ ID NO: 1 has a sequence which is at least 70% identical to SEQ ID NO: 1, wherein the residue in position 12 is not an R residue.

The term "nucleotide sequence" as used herein may also be denoted by the term "nucleic acid sequence". Below, the expression "gene" is sometimes used, which is a nucleotide sequence encoding for a polypeptide.

The term "polynucleotide" as used herein refers to a compound consisting of a contiguous sequence of nucleotides linked by covalent bonds.

The term "fusion polypeptide" as used herein relates to a polypeptide obtained after fusion of two or more polypeptides, i.e. arrangement in-frame as part of the same contiguous sequence of amino acid residues. Fusion can be direct, i.e. with no additional amino acid residues between the two polypeptides, or achieved via a linker. Such a linker may be used to improve performance and/or alter the functionality.

The term "domain" as used herein, which may also be denoted "region", refers to a contiguous sequence of amino acid residues that has a specific function, such as binding to a ligand and/or conferring instability, or to a contiguous sequence of nucleotides coding for a contiguous sequence of amino acid residues that has a specific function. The term "domain" may also refer to an independently folding unit within a protein.

The term "gene therapy" as used herein refers to the insertion of genes into a subject's cells and tissues to treat a disease.

The term "therapeutic" in relation to a polypeptide, a protein or a polynucleotide refers to the ability of the polypeptide, the protein or the polypeptide or protein encoded by the polynucleotide to exert a therapeutic activity.

The term "operatively linked" as used herein refers to a mutant polypeptide and a polypeptide of interest linked in such a manner that when the mutant polypeptide is stable and thus active, i.e. in the presence of a ligand as described herein, the polypeptide of interest is also stable and active, while in the absence of a ligand, the destabilisation of the mutant polypeptide leads also to the destabilisation of the polypeptide of interest.

Throughout the present disclosure, mutations will be designated as follows: XNZ, where X is the one-letter amino acid code for the amino acid present in the DHFR sequence (s) from *Escherichia coli* as set forth in SEQ ID NO: 1 at position N, while Z is the one-letter amino acid code for the amino acid substituting X at position N in the mutant.

DETAILED DESCRIPTION OF THE INVENTION

The invention is as described in the claims.

The present disclosure relates to a method for conditionally stabilising a fusion polypeptide. The fusion polypeptide is a fusion of a mutant polypeptide derived from DHFR and of a polypeptide of interest, of which it is desirable to tightly control the activity. The mutant polypeptide can be bound by a DHFR inhibitor. In the absence of the inhibitor, the mutant polypeptide, and consequently also the fusion polypeptide and the polypeptide of interest, is not active. In the presence of DHFR inhibitor, the mutant polypeptide is bound by the inhibitor, which binding results in stabilisation of the mutant polypeptide and thus also of the fusion polypeptide and of the polypeptide of interest. As a consequence, the polypeptide of interest is active and/or functional in the presence of ligand only. This system can be used as a safety switch in gene therapy, where the administration of a ligand is necessary for the transgene to lead to a functional and/or active protein. In the absence of ligand, the transgene is expressed but leads to an inactive protein. In some embodiments, the present system has a dose-dependent response, and can thus be taken advantage of to precisely tune the extent of activation of the polypeptide of interest, by adjusting the amount of ligand. This can be desirable in order to personalise a treatment depending on the subject, the disorder to be treated, the nature of the polypeptide of interest, or the need to vary the dose of a polypeptide of interest over time.

DHFR is a 159-residue enzyme catalyzing the reduction of dihydrofolate to tetrahydrofolate, a cofactor that is essential for several steps in prokaryotic primary metabolism (Schnell et al., 2004). Unless otherwise specified, the term "DHFR" as used herein refers to *E. coli* DHFR.

Numerous inhibitors of DHFR have been developed as drugs (Schweitzer et al., 1990), and one such inhibitor, trimethoprim (TMP), inhibits DHFR from *E. coli* (ecDHFR) much more potently than mammalian DHFR (Matthews et al., 1985). This large therapeutic window renders TMP "biologically silent" in mammalian cells, which is particularly relevant in the context of gene therapy. The specificity of the ecDHFR-TMP interaction, coupled with the commercial availability and attractive pharmacological properties of TMP, makes this protein-ligand pair ideal for development of a conditional protein stability system as described herein.

Mutant Polypeptide Derived from DHFR

The present disclosure provides mutant polypeptides derived from DHFR as set forth in SEQ ID NO: 1 (corresponding to wild type *E. coli* DHFR) and in SEQ ID NO: 2 in at least one of the following positions: R12, N18, M42, Y100, D122, P126, D127, W133 and/or F153, with the proviso that the mutant polypeptide does not differ from SEQ ID NO: 1 and SEQ ID NO: 2 only by a Y100I mutation. As will be seen from the examples, such mutant polypeptides are particularly advantageous in conditional protein stability systems and have applications e.g. in gene therapy. The mutant polypeptides can be fused to a protein of interest, of which the activity can then be modulated by the presence or absence of a ligand, e.g. a DHFR inhibitor. The mutant polypeptides provided herein have the ability to allow for sufficient stability, and hence activity, of the protein of interest in the presence of a DHFR inhibitor, while at the same time efficiently shutting down the protein's activity in the absence of DHFR inhibitor.

In some embodiments, the mutant polypeptide derived from DHFR as set forth in SEQ ID NO: 1 and SEQ ID NO: 2 has at least 70% identity to SEQ ID NO: 1, such as at least 75% identity, such as 80% identity, such as at least 85% identity, such as at least 90% identity, such as at least 95% identity, such as at least 96% identity, such as at least 97% identity, such as at least 98% identity, such as at least 99% identity to SEQ ID NO: 1. In other embodiments, the mutant polypeptide derived from DHFR as set forth in SEQ ID NO: 1 and SEQ ID NO: 2 has at least 70% identity to SEQ ID NO: 2, such as at least 75% identity, such as 80% identity, such as at least 85% identity, such as at least 90% identity, such as at least 95% identity, such as at least 96% identity, such as at least 97% identity, such as at least 98% identity, such as at least 99% identity to SEQ ID NO: 2.

In some embodiments, the mutant polypeptide differs from DHFR as set forth in SEQ ID NO: 1 by the presence of at least one mutation in position R12 and has at least 70% identity to SEQ ID NO: 1, such as at least 75% identity, such as at least 80% identity, such as at least 85% identity, such as at least 90% identity, such as at least 95% identity, such as at least 96% identity, such as at least 97% identity, such as at least 98% identity, such as at least 99% identity to SEQ ID NO: 1. In some embodiments, the mutant polypeptide differs from DHFR as set forth in SEQ ID NO: 1 by the presence of at least one mutation in position N18 and has at least 70% identity to SEQ ID NO: 1, such as at least 75% identity, such as at least 80% identity, such as at least 85% identity, such as at least 90% identity, such as at least 95% identity, such as at least 96% identity, such as at least 97% identity, such as at least 98% identity, such as at least 99% identity to SEQ ID NO: 1. In some embodiments, the mutant polypeptide differs from DHFR as set forth in SEQ ID NO: 1 by the presence of at least one mutation in position M42 and has at least 70% identity to SEQ ID NO: 1, such as at least 75% identity, such as at least 80% identity, such as at least 85% identity, such as at least 90% identity, such as at least 95% identity, such as at least 96% identity, such as at least 97% identity, such as at least 98% identity, such as at least 99% identity to SEQ ID NO: 1. In some embodiments, the mutant polypeptide differs from DHFR as set forth in SEQ ID NO: 1 by the presence of at least one mutation in position Y100, and has at least 70% identity to SEQ ID NO: 1, such as at least 75% identity, such as at least 80% identity, such as at least 85% identity, such as at least 90% identity, such as at least 95% identity, such as at least 96% identity, such as at least 97% identity, such as at least 98% identity, such as at least 99% identity to SEQ ID NO: 1. In some embodiments, the mutant polypeptide differs from DHFR as set forth in SEQ ID NO: 1 by the presence of at least one mutation in position D122 and has at least 70% identity to SEQ ID NO: 1, such as at least 75% identity, such as at least 80% identity, such as at least 85% identity, such as at least 90% identity, such as at least 95% identity, such as at least 96% identity, such as at least 97% identity, such as at least 98% identity, such as at least 99% identity to SEQ ID NO: 1. In some embodiments, the mutant polypeptide differs from DHFR as set forth in SEQ ID NO: 1 by the presence of at least one mutation in position P126 and has at least 70% identity to SEQ ID NO: 1, such as at least 75% identity, such as at least 80% identity, such as at least 85% identity, such as at least 90% identity, such as at least 95% identity, such as at least 96% identity, such as at least 97% identity, such as at least 98% identity, such as at least 99% identity to SEQ ID NO: 1. In some embodiments, the mutant polypeptide differs from DHFR as set forth in SEQ ID NO: 1 by the presence of at least one mutation in position D127 and has at least 70% identity to SEQ ID NO: 1, such as at least 75% identity, such as at least 80% identity, such as at least 85% identity, such as at least 90% identity, such as at least 95% identity, such as at least 96% identity, such as at least 97% identity, such as at least 98% identity, such as at least 99% identity to SEQ ID NO: 1. In some embodiments, the mutant polypeptide differs from DHFR as set forth in SEQ ID NO: 1 by the presence of at least one mutation in position W133 and has at least 70% identity to SEQ ID NO: 1, such as at least 75% identity, such as at least 80% identity, such as at least 85% identity, such as at least 90% identity, such as at least 95% identity, such as at least 96% identity, such as at least 97% identity, such as at least 98% identity, such as at least 99% identity to SEQ ID NO: 1. In some embodiments, the mutant polypeptide differs from DHFR as set forth in SEQ ID NO: 1 by the presence of at least one mutation in position F153 and has at least 70% identity to SEQ ID NO: 1, such as at least 75% identity, such as at least 80% identity, such as at least 85% identity, such as at least 90% identity, such as at least 95% identity, such as at least 96% identity, such as at least 97% identity, such as at least 98% identity, such as at least 99% identity to SEQ ID NO: 1. In some embodiments, the mutant polypeptide differs from DHFR as set forth in SEQ ID NO: 1 by the presence of at least one mutation in a position selected from the group consisting of W133, F153 or F153 and has at least 70% identity to SEQ ID NO: 1, such as at least 75% identity, such as at least 80% identity, such as at least 85% identity, such as at least 90% identity, such as at least 95% identity, such as at least 96% identity, such as at least 97% identity, such as at least 98% identity, such as at least 99% identity to SEQ ID NO: 1.

In some embodiments, the mutant polypeptide differs from DHFR as set forth in SEQ ID NO: 2 by the presence of at least one mutation in position R12 and has at least 70% identity to SEQ ID NO: 2, such as at least 75% identity, such as at least 80% identity, such as at least 85% identity, such as at least 90% identity, such as at least 95% identity, such as at least 96% identity, such as at least 97% identity, such as at least 98% identity, such as at least 99% identity to SEQ ID NO: 2. In some embodiments, the mutant polypeptide differs from DHFR as set forth in SEQ ID NO: 2 by the presence of at least one mutation in position N18 and has at least 70% identity to SEQ ID NO: 2, such as at least 75% identity, such as at least 80% identity, such as at least 85% identity, such as at least 90% identity, such as at least 95% identity, such as at least 96% identity, such as at least 97% identity, such as at least 98% identity, such as at least 99% identity to SEQ ID NO: 2. In some embodiments, the mutant polypeptide differs from DHFR as set forth in SEQ ID NO: 2 by the presence of at least one mutation in position M42 and has at least 70% identity to SEQ ID NO: 2, such as at least 75% identity, such as at least 80% identity, such as at least 85% identity, such as at least 90% identity, such as at least 95% identity, such as at least 96% identity, such as at least 97% identity, such as at least 98% identity, such as at least 99% identity to SEQ ID NO: 2. In some embodiments, the mutant polypeptide differs from DHFR as set forth in SEQ ID NO: 2 by the presence of at least one mutation in position Y100, and has at least 70% identity to SEQ ID NO: 2, such as at least 75% identity, such as at least 80% identity, such as at least 85% identity, such as at least 90% identity, such as at least 95% identity, such as at least 96% identity, such as at least 97% identity, such as at least 98% identity, such as at least 99% identity to SEQ ID NO: 2. In some embodiments, the mutant polypeptide differs from DHFR as set forth in SEQ ID NO: 2 by the presence of at least one mutation in position D122 and has at least 70% identity to SEQ ID NO: 2, such as at least 75% identity, such as at least 80% identity, such as at least 85% identity, such as at least 90% identity, such as at least 95% identity, such as at least 96% identity, such as at least 97% identity, such as at least 98% identity, such as at least 99% identity to SEQ ID NO: 2. In some embodiments, the mutant polypeptide differs from DHFR as set forth in SEQ ID NO: 2 by the presence of at least one mutation in position P126 and has at least 70% identity to SEQ ID NO: 2, such as at least 75% identity, such as at least 80% identity, such as at least 85% identity, such as at least 90% identity, such as at least 95% identity, such as at least 96% identity, such as at least 97% identity, such as at least 98% identity, such as at least 99% identity to SEQ ID NO: 2. In some embodiments, the mutant polypeptide differs from DHFR as set forth in SEQ ID NO: 2 by the presence of at least one mutation in position D127 and has at least 70% identity to SEQ ID NO: 2, such as at least 75% identity, such as at least 80% identity, such as at least 85% identity, such as at least 90% identity, such as at least 95% identity, such as at least 96% identity, such as at least 97% identity, such as at least 98% identity, such as at least 99% identity to SEQ ID NO: 2. In some embodiments, the mutant polypeptide differs from DHFR as set forth in SEQ ID NO: 2 by the presence of at least one mutation in position W133 and has at least 70% identity to SEQ ID NO: 2, such as at least 75% identity, such as at least 80% identity, such as at least 85% identity, such as at least 90% identity, such as at least 95% identity, such as at least 96% identity, such as at least 97% identity, such as at least 98% identity, such as at least 99% identity to SEQ ID NO: 2. In some embodiments, the mutant polypeptide differs from DHFR as set forth in SEQ ID NO: 2 by the presence of at least one mutation in position F153 and has at least 70% identity to SEQ ID NO: 2, such as at least 75% identity, such as at least 80% identity, such as at least 85% identity, such as at least 90% identity, such as at least 95% identity, such as at least 96% identity, such as at least 97% identity, such as at least 98% identity, such as at least 99% identity to SEQ ID NO: 2. In some embodiments, the mutant polypeptide differs from DHFR as set forth in SEQ ID NO: 2 by the presence of at least one mutation in a position selected from the group consisting of W133, F153 or F153 and has at least 70% identity to SEQ ID NO: 2, such as at least 75% identity, such as at least 80% identity, such as at least 85% identity, such as at least 90% identity, such as at least 95% identity, such as at least 96% identity, such as at least 97% identity, such as at least 98% identity, such as at least 99% identity to SEQ ID NO: 2.

In some embodiments, the mutant polypeptide differs from DHFR as set forth in SEQ ID NO: 1 and in SEQ ID NO: 2 by the presence of at least one mutation in position R12. In some embodiments, the mutant polypeptide differs from DHFR as set forth in SEQ ID NO: 1 and in SEQ ID NO: 2 by the presence of at least one mutation in position N18. In some embodiments, the mutant polypeptide differs from DHFR as set forth in SEQ ID NO: 1 and in SEQ ID NO: 2 by the presence of at least one mutation in position M42. In some embodiments, the mutant polypeptide differs from DHFR as set forth in SEQ ID NO: 1 and in SEQ ID NO: 2 by the presence of at least one mutation in position Y100. In some embodiments, the mutant polypeptide differs from DHFR as set forth in SEQ ID NO: 1 and in SEQ ID NO: 2 by the presence of at least one mutation in position D122. In some embodiments, the mutant polypeptide differs from DHFR as set forth in SEQ ID NO: 1 and in SEQ ID NO: 2 by the presence of at least one mutation in position P126. In some embodiments, the mutant polypeptide differs from DHFR as set forth in SEQ ID NO: 1 and in SEQ ID NO: 2 by the presence of at least one mutation in position D127. In some embodiments, the mutant polypeptide differs from DHFR as set forth in SEQ ID NO: 1 and in SEQ ID NO: 2 by the presence of at least one mutation in position W133. In some embodiments, the mutant polypeptide differs from DHFR as set forth in SEQ ID NO: 1 and in SEQ ID NO: 2 by the presence of at least one mutation in position F153. In some embodiments, the mutant polypeptide differs from DHFR as set forth in SEQ ID NO: 1 and in SEQ ID NO: 2 by the presence of at least one mutation in a position selected from the group consisting of W133, F153 or F153.

In some embodiments, the mutant polypeptide differs from DHFR as set forth in SEQ ID NO: 1 and in SEQ ID NO: 2 by the presence of at least an R12A mutation. In some embodiments, the mutant polypeptide differs from DHFR as set forth in SEQ ID NO: 1 and in SEQ ID NO: 2 by the presence of at least an N18T mutation. In some embodiments, the mutant polypeptide differs from DHFR as set forth in SEQ ID NO: 1 and in SEQ ID NO: 2 by the presence of at least an M42A mutation. In some embodiments, the mutant polypeptide differs from DHFR as set forth in SEQ ID NO: 1 and in SEQ ID NO: 2 by the presence of at least an M42G mutation. In some embodiments, the mutant polypeptide differs from DHFR as set forth in SEQ ID NO: 1 and in SEQ ID NO: 2 by the presence of at least a Y100E mutation. In some embodiments, the mutant polypeptide differs from DHFR as set forth in SEQ ID NO: 1 and in SEQ ID NO: 2 by the presence of at least a D122A mutation. In some embodiments, the mutant polypeptide differs from DHFR as set forth in SEQ ID NO: 1 and in SEQ ID NO: 2 by the presence of at least a P126Y mutation. In some embodiments, the mutant polypeptide differs from DHFR as set forth in SEQ ID NO: 1 and in SEQ ID NO: 2 by the presence of at least a P126R mutation. In some embodiments, the mutant polypeptide differs from DHFR as set forth in SEQ ID NO: 1 and in SEQ ID NO: 2 by the presence of at least a P126D mutation. In some embodiments, the mutant polypeptide differs from DHFR as set forth in SEQ ID NO: 1 and in SEQ ID NO: 2 by the presence of at least a D127A mutation. In some embodiments, the mutant polypeptide differs from DHFR as set forth in SEQ ID NO: 1 and in SEQ ID NO: 2 by the presence of at least a D127N mutation. In some embodiments, the mutant polypeptide differs from DHFR as set forth in SEQ ID NO: 1 and in SEQ ID NO: 2 by the presence of at least a W133A mutation. In some embodiments, the mutant polypeptide differs from DHFR as set forth in SEQ ID NO: 1 and in SEQ ID NO: 2 by the presence of at least an F153G mutation. In some embodiments, the mutant polypeptide differs from DHFR as set forth in SEQ ID NO: 1 and in SEQ ID NO: 2 by the presence of at least an F153A mutation. In some embodiments, the mutant polypeptide differs from DHFR as set forth in SEQ ID NO: 1 and in SEQ ID NO: 2 by the presence of at least an F153D mutation. In some preferred embodiments, the mutant polypeptide differs from DHFR as set forth in SEQ ID NO: 1 and in SEQ ID NO: 2 by the presence of at least one mutation selected from the group consisting of W133A, F153G or F153D.

In some embodiments, the mutant polypeptide does not differ from SEQ ID NO: 1 and SEQ ID NO: 2 solely by the presence of a Y100I mutation.

In one embodiment, the mutant polypeptide is an R12A mutant. In another embodiment, the mutant polypeptide is an N18T mutant. In another embodiment, the mutant polypeptide is an M42A mutant. In another embodiment, the mutant polypeptide is an M42G mutant. In another embodiment, the mutant polypeptide is a Y100E mutant. In another embodiment, the mutant polypeptide is a D122A mutant. In another embodiment, the mutant polypeptide is a P126Y mutant. In another embodiment, the mutant polypeptide is a P126D mutant. In another embodiment, the mutant polypeptide is a P126R mutant. In another embodiment, the mutant polypeptide is a D127A mutant. In another embodiment, the mutant polypeptide is a D127N mutant. In another embodiment, the mutant polypeptide is a W133A mutant. In another embodiment, the mutant polypeptide is an F153G mutant. In another embodiment, the mutant polypeptide is an F153A mutant. In another embodiment, the mutant polypeptide is an F153D mutant. In particular embodiments, the mutant polypeptide is an M42A mutant, an M42G mutant, a Y100E mutant, a P126Y mutant, a P126R mutant, a P126D mutant, a W133A mutant, an F153G mutant, an F153A mutant or an F153D mutant.

In some embodiments, the mutant polypeptide comprises two mutations. In one embodiment, the mutant polypeptide is an R12A Y100I mutant. In another embodiment, the mutant is an N18T Y100I mutant. In another embodiment, the mutant polypeptide is a Y100I D122A mutant. In another embodiment, the mutant polypeptide is a Y100I D127N mutant. In another embodiment, the mutant polypeptide is a Y100I W133A mutant. In another embodiment, the mutant polypeptide is a Y100I F153D mutant. In another embodiment, the mutant polypeptide is a Y100I F153G mutant. In another embodiment, the mutant polypeptide is an R12A Y100E mutant. In another embodiment, the mutant polypeptide is an N18T Y100E mutant. In another embodiment, the mutant polypeptide is an M42A Y100E mutant. In another embodiment, the mutant polypeptide is an M42G Y100E mutant. In another embodiment, the mutant polypeptide is a Y100E D127A mutant. In another embodiment, the mutant polypeptide is a Y100E D127N mutant. In another embodiment, the mutant polypeptide is a Y100E P126Y mutant. In another embodiment, the mutant polypeptide is a Y100E P126D mutant. In another embodiment, the mutant polypeptide is a Y100E P126R mutant. In another embodiment, the mutant polypeptide is a Y100E W133A mutant. In another embodiment, the mutant polypeptide is a Y100E F153D mutant. In another embodiment, the mutant polypeptide is a Y100E F153G mutant. In particular embodiments, the mutant polypeptide is an N18T Y100I mutant, a Y100I D127N mutant, or an M42A Y100E mutant.

In some embodiments, the mutant polypeptide comprises three mutations. In one embodiment, the mutant polypeptide is an N18T Y100I D122A mutant. In another embodiment, the mutant polypeptide is an N18T Y100E D122A mutant.

In some embodiments, the mutant polypeptide does not differ from the parent sequence by more than five residues, such as by more than four residues, such as by more than three residues, such as by more than two residues, such as by more than one residue. Some mutant polypeptides of the present disclosure do not differ from SEQ ID NO: 1 by more than five residues. Other mutant polypeptides of the present disclosure do not differ from SEQ ID NO: 1 by more than four residues. Other mutant polypeptides of the present disclosure do not differ from SEQ ID NO: 1 by more than three residues. Other mutant polypeptides of the present disclosure do not differ from SEQ ID NO: 1 by more than two residues. Other mutant polypeptides of the present disclosure do not differ from SEQ ID NO: 1 by more than one residue. Preferably, the mutant polypeptide does not differ from SEQ ID NO: 1 solely by a Y100I mutation. Some mutant polypeptides of the present disclosure do not differ from SEQ ID NO: 2 by more than five residues. Other mutant polypeptides of the present disclosure do not differ from SEQ ID NO: 2 by more than four residues. Other mutant polypeptides of the present disclosure do not differ from SEQ ID NO: 2 by more than three residues. Other mutant polypeptides of the present disclosure do not differ from SEQ ID NO: 2 by more than two residues. Other mutant polypeptides of the present disclosure do not differ from SEQ ID NO: 2 by more than one residue. Preferably, the mutant polypeptide does not differ from SEQ ID NO: 2 solely by a Y100I mutation.

Besides the specific embodiments listed herein above, the mutant polypeptide may comprise further mutations as described below.

Partial or Total Removal of Side Chain at a Given Position

Without being bound by theory, some mutations in the above-mentioned positions which replace an amino acid having a side chain with an amino acid having a shorter side chain or no side chain appear particularly advantageous. Accordingly, in some embodiments the mutant polypeptide differs from SEQ ID NO: 1 and SEQ ID NO:2 by the presence of a mutation in at least one of R12, N18, M42, Y100, D122, P126, D127, W133 and/or F153, wherein the mutation is a substitution by a G residue or by an A residue. Substitution by a glycine residue completely removes the side chain at a given position, while substitution by an alanine residue partly removes or shortens the side chain at a given position.

Hence, in some preferred embodiments, the mutant polypeptide differs from DHFR as set forth in SEQ ID NO: 1 and in SEQ ID NO: 2 by the presence of one mutation selected from the group consisting of R12A, R12G, N18A, N18G, M42A, M42G, D122A, D122G, P126A, P126G, D127A, D127G, W133A, W133G, F153A and F153G, preferably W133A, F153G, R12A, M42A or F153A.

Additional Mutations

The mutant polypeptide may further comprise one or more additional mutations. These may confer further advantageous properties to the fusion polypeptides comprising the mutant polypeptide fused to a polypeptide of interest as described herein below.

Thus in some embodiments, the mutant polypeptide differs from SEQ ID NO: 1 and SEQ ID NO: 2 in at least one of positions R12, N18, M42, Y100, D122, P126, D127, W133 and/or F153, and in a further position.

In some embodiments, the mutant polypeptide further comprises a mutation at position Y100, such as Y100E or Y100I, preferably Y100E. In some embodiments, the mutant polypeptide is an M42A Y100E mutant. In some embodiments, the mutant polypeptide is an N18T Y100I mutant. In some embodiments, the mutant is a D127N Y100I mutant.

Further mutations located in the TMP binding pocket of DHFR may also be advantageous. The TMP binding pocket is the pocket formed by DHFR which interacts with TMP. The following residues are known to be involved (Roth et al., 1987, J Med Chem. 1987 February; 30(2):348-56): M20, L28, F31, T46, S49, 150 and L54.

Polynucleotides and Vectors

Also provided herein are polynucleotides encoding any of the mutant polypeptides described herein above, as well as vectors comprising such polynucleotides. Such vectors may comprise several mutant polypeptides as described herein.

Fusion Polypeptides

The mutant polypeptides described herein above are useful in fusion polypeptides, where they are operatively linked to one or more polypeptides of interest. In the absence of ligand, the mutant polypeptide is unstable, and this in turn results in the polypeptide of interest being unstable and hence inactive. This is the “off” configuration. In the presence of ligand, the mutant polypeptide is stable, and the polypeptide of interest is also stable and hence active. The addition of ligand can thus be used as safety switch preventing the unwanted activation of a polypeptide of interest, e.g. in the context of gene therapy, in the absence of ligand.

The present disclosure thus provides fusion polypeptides comprising a mutant polypeptide as described herein operatively linked to a polypeptide of interest. The mutant polypeptides are derived from DHFR as set forth in SEQ ID NO: 1 (corresponding to wild type *E. coli* DHFR) and in SEQ ID NO: 2 in at least one of the following positions: R12, N18, M42, Y100, D122, P126, D127, W133 and/or F153, with the proviso that the mutant polypeptide does not differ from SEQ ID NO: 1 and SEQ ID NO: 2 only by a Y100I mutation, as described herein above. In some embodiments, the mutant polypeptide derived from DHFR as set forth in SEQ ID NO: 1 and SEQ ID NO: 2 has at least 70% identity to SEQ ID NO: 1, such as at least 75% identity, such as 80% identity, such as at least 85% identity, such as at least 90% identity, such as at least 95% identity, such as at least 96% identity, such as at least 97% identity, such as at least 98% identity, such as at least 99% identity to SEQ ID NO: 1. In other embodiments, the mutant polypeptide derived from DHFR as set forth in SEQ ID NO: 1 and SEQ ID NO: 2 has at least 70% identity to SEQ ID NO: 2, such as at least 75% identity, such as 80% identity, such as at least 85% identity, such as at least 90% identity, such as at least 95% identity, such as at least 96% identity, such as at least 97% identity, such as at least 98% identity, such as at least 99% identity to SEQ ID NO: 2.

In some embodiments, it may be desirable to be able to monitor the actual expression of the fusion polypeptides. Accordingly, in some embodiments, the fusion polypeptide may also comprise a reporter polypeptide. The reporter polypeptide may be operatively linked to the mutant polypeptide or to the polypeptide of interest by one of its termini, or it may be linked to both the mutant polypeptide and to the polypeptide of interest, at each of its termini.

The reporter polypeptide may be any reporter polypeptide known in the art and suitable for monitoring purposes. In some embodiments, the reporter polypeptide is a fluorescent protein, of which the activity/stability can be monitored by fluorescence microscopy methods as is known to the person of skill in the art. In other embodiments, the reporter polypeptide is an enzyme, of which the activity can be measured by enzymatic assays. In yet other embodiments, the reporter polypeptide is an affinity tag, of which the activity can be measured as is known in the art.

Preferably, the fusion polypeptides described herein are such that the mutant polypeptide is operatively linked to the N-terminal end of the polypeptide of interest. However, fusion polypeptides where the mutant polypeptide is further operatively linked to the C-terminal end of a second or additional polypeptide of interest are also envisaged.

Accordingly, in some embodiments, the mutant polypeptide may be operatively linked to the N-terminal end of a polypeptide of interest and may be operatively further linked to the C-terminal end of a further polypeptide of interest. Such fusion polypeptides thus may allow for conditional stability of two polypeptides of interest at once.

It will be understood that the polypeptide of interest or the further polypeptide of interest linked to the C-terminal end or the N-terminal end of the mutant polypeptide may itself further be operatively linked to a further polypeptide of interest or to a reporter polypeptide in its other terminal end.

The person of skill in the art knows how to design linkers that are suitable for operatively linking the polypeptide of interest to the mutant polypeptide.

Polypeptide of Interest

Any of the above mentioned polypeptides of interest, i.e. the polypeptide of interest to which the mutant polypeptide is fused, the further polypeptide of interest or any additional polypeptide of interest, may be any polypeptide for which it is desirable to conditionally control the stability, and hence activity, e.g. in a host cell. Preferably, the polypeptide of interest is a therapeutic polypeptide, a reporter polypeptide, an enzyme or a transcription factor.

Non-limiting examples of therapeutic polypeptides include transcription factors, neurotrophic factors, cell surface receptors, ATPases, cyclin-dependent kinase inhibitors and antibodies having a therapeutic effect when active in a host cell, e.g. of a subject in need of treatment for a disorder.

Additional Features

The fusion polypeptides described herein may further comprise additional features. In some cases, it may be desirable to include a signal peptide, e.g. a signal peptide capable of causing secretion of the fusion polypeptide from a cell. This would allow for secretion of a polypeptide of interest in a recombinant host, e.g. a microbial cell such as a yeast cell or a bacterial cell. It may be desirable to include a cleavage signal so that only the polypeptide of interest, without the mutant polypeptide, is secreted, or so that the polypeptide of interest can be isolated without being fused to the mutant polypeptide. In other cases, it may be relevant to include a subcellular localisation signal such as a nuclear localisation signal capable of causing import of the fusion polypeptide into the nucleus or some other compartment of a cell; this may be particularly relevant if the polypeptide of interest is a transcription factor. The skilled person knows how to design a fusion polypeptide so that it comprises such signal peptides.

Polynucleotides and Vectors

Also provided herein are polynucleotides encoding any of the fusion polypeptides described herein above, as well as vectors comprising such polynucleotides. Such vectors may comprise several fusion polypeptides as described herein.

Gene Expression System

Also provided herein is a gene expression system comprising a polynucleotide encoding a fusion polypeptide as described herein. The gene expression system of the present invention may comprise a vector comprising a polynucleotide encoding a fusion polypeptide as described herein. In some embodiments, the gene expression system is suitable for administration in the context of gene therapy to a subject in need thereof.

Broadly, gene therapy seeks to transfer new genetic material to the cells of a patient with resulting therapeutic benefit to the patient. Such benefits include treatment or prophylaxis of a broad range of diseases, disorders and other conditions.

Ex vivo gene therapy approaches involve modification of isolated cells (including but not limited to stem cells, neural and glial precursor cells, and fetal stem cells), which are then infused, grafted or otherwise transplanted into the patient. See, e.g., U.S. Pat. Nos. 4,868,116, 5,399,346 and 5,460,959. In vivo gene therapy seeks to directly target host patient tissue in vivo.

Viruses useful as gene transfer vectors include papovavirus, adenovirus, vaccinia virus, adeno-associated virus, herpesvirus, and retroviruses. Suitable retroviruses include the group consisting of HIV, SIV, FIV, EIAV, MoMLV. A further group of suitable retroviruses includes the group consisting of HIV, SIV, FIV, EAIV, CIV. Another group of preferred virus vectors includes the group consisting of alphavirus, adenovirus, adeno associated virus, baculovirus, HSV, coronavirus, Bovine papilloma virus, Mo-MLV, preferably adeno associated virus (AAV).

Lentiviruses and adeno-associated viruses are preferred vectors for use in the treatment of disorders of the central nervous system. Both types of viruses can integrate into the genome without cell divisions, and both types have been tested in pre-clinical animal studies for indications of the nervous system, in particular the central nervous system.

Methods for preparation of AAV are described in the art, e.g. U.S. Pat. No. 5,677,158. U.S. Pat. Nos. 6,309,634 and 6,683,058 describe examples of delivery of AAV to the central nervous system.

A lentiviral vector is a replication-defective lentivirus particle. Such a lentivirus particle can be produced from a lentiviral vector comprising a 5' lentiviral LTR, a tRNA binding site, a packaging signal, a promoter operably linked to a polynucleotide signal encoding said fusion protein, an origin of second strand DNA synthesis and a 3' lentiviral LTR. Methods for preparation and in vivo administration of lentivirus to neural cells are described in US 20020037281 (Methods for transducing neural cells using lentiviral vectors).

Retroviral vectors are the vectors most commonly used in human clinical trials, since they can carry 7-8 kb or heterologous DNA and since they have the ability to infect cells and have their genetic material stably integrated into the host cell with high efficiency. See, e.g., WO 95/30761; WO 95/24929. Oncovirinae require at least one round of target cell proliferation for transfer and integration of exogenous nucleic acid sequences into the patient. Retroviral vectors integrate randomly into the patient's genome. Retroviruses can be used to target stem cells of the nervous system as very few cell divisions take place in other cells of the nervous system (in particular the CNS).

Three classes of retroviral particles have been described; ecotropic, which can infect murine cells efficiently, and amphotropic, which can infect cells of many species. The third class includes xenotrophic retrovirus which can infect cells of another species than the species which produced the virus. Their ability to integrate only into the genome of dividing cells has made retroviruses attractive for marking cell lineages in developmental studies and for delivering therapeutic or suicide genes to cancers or tumors.

For use in human patients, the retroviral vectors must be replication defective. This prevents further generation of infectious retroviral particles in the target tissue—instead the replication defective vector becomes a "captive" transgene stable incorporated into the target cell genome. Typically in replication defective vectors, the gag, env, and pol genes have been deleted (along with most of the rest of the viral genome). Heterologous DNA is inserted in place of the deleted viral genes. The heterologous genes may be under the control of the endogenous heterologous promoter, another heterologous promoter active in the target cell, or the retroviral 5' LTR (the viral LTR is active in diverse tissues). Typically, retroviral vectors have a transgene capacity of about 7-8 kb.

Replication defective retroviral vectors require provision of the viral proteins necessary for replication and assembly in trans, from, e.g., engineered packaging cell lines. It is important that the packaging cells do not release replication competent virus and/or helper virus. This has been achieved by expressing viral proteins from RNAs lacking the ψ signal, and expressing the gag/pol genes and the env gene from separate transcriptional units. In addition, in some retroviruses of second or third generation, the 5' LTR's have been replaced with non-viral promoters controlling the expression of these genes, and the 3' promoter has been minimised to contain only the proximal promoter. These designs minimize the possibility of recombination leading to production of replication competent vectors, or helper viruses.

Construction of vectors for use in the methods disclosed herein may be accomplished using conventional techniques which do not require detailed explanation to one of ordinary skill in the art. For review, however, those of ordinary skill may wish to consult Maniatis et al., in Molecular Cloning: A Laboratory Manual, Cold Spring Harbor Laboratory, (NY 1982). Expression vectors may be used for generating producer cells for recombinant production of a polypeptide of interest such as a therapeutic peptide, for example for medical use, and for generating therapeutic cells secreting a polypeptide of interest for naked or encapsulated therapy.

Briefly, construction of recombinant expression vectors employs standard ligation techniques. For analysis to confirm correct sequences in vectors constructed, the genes are sequenced using, for example, Sanger sequencing or next generation sequencing or other suitable methods which will be known to those skilled in the art.

Size separation of cleaved fragments is performed using conventional gel electrophoresis as described, for example, by Maniatis, et al., (Molecular Cloning, pp. 133-134,1982).

For generation of efficient expression vectors, these should contain regulatory sequences necessary for expression of the encoded gene in the correct reading frame. Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many genes consists of the promoter and in some cases enhancer or regulator elements (Banerji et al., Cell 27: 299 (1981); Corden et al., Science 209: 1406 (1980); and Breathnach and Chambon, Ann. Rev. Biochem. 50: 349 (1981)). For retroviruses, control elements involved in the replication of the retroviral genome reside in the long terminal repeat (LTR) (Weiss et al., eds., The molecular biology of tumor viruses: RNA tumor viruses, Cold Spring Harbor Laboratory, (NY 1982)). Moloney murine leukemia virus (MLV) and Rous sarcoma virus (RSV) LTRs contain promoter and enhancer sequences (Jolly et al., Nucleic Acids Res. 11: 1855 (1983); Capecchi et al., In: Enhancer and eukaryotic gene expression, Gulzman and Shenk, eds., pp. 101-102, Cold Spring Harbor Laboratories (NY 1991). Other potent promoters include those derived from cytomegalovirus (CMV) and other wild-type viral promoters.

Promoter and enhancer regions of a number of non-viral promoters have also been described (Schmidt et al., Nature 314: 285 (1985); Rossi and deCrombrugghe, Proc. Natl. Acad. Sci. USA 84: 5590-5594 (1987)). Methods for maintaining and increasing expression of transgenes in quiescent cells include the use of promoters including collagen type I (1 and 2) (Prockop and Kivirikko, N. Eng. J. Med. 311: 376 (1984); Smith and Niles, Biochem. 19: 1820 (1980); de Wet et al., J. Biol. Chem., 258: 14385 (1983)), SV40 and LTR promoters. Promoters and other regulatory elements of the present invention are described in further detail herein below.

In one embodiment the expression system is a vector, such as a viral vector, e.g. a viral vector expression system.

In another embodiment, the expression system is a plasmid vector expression system.

In yet another embodiment the expression system is based on a synthetic vector.

In yet another embodiment the expression system is a cosmid vector or an artificial chromosome.

In one embodiment the expression system according to the present disclosure is a viral vector selected from the group consisting of an adeno associated vector (AAV), adenoviral vector and retroviral vector.

In one embodiment the vector is an integrating vector. In another embodiment the vector is a non-integrating vector.

In one embodiment the vector of the present disclosure is a minimally integrating vector.

In one embodiment the expression system according to the present disclosure is an adeno associated vector (AAV).

AAV vectors can be prepared using two major principles, transfection of human cell line monolayer culture or free floating insect cells. Monolayer cell cultures are transfected through calcium phosphate precipitation, lipofection or other means with a mix of two or three plasmid preparations containing a transfer plasmid with the vector genome and one or two helper plasmids containing the necessary genes for vector capsid synthesis. For insect cell cultures, this process is normally replaced by transfection of the cells using baculovirus constructs that contain the same functions. The cells, supernatant or both are then collected for purification and concentration of the vector. This can be achieved through any combination of caesium chloride or iodixanol gradient purification, ion exchange chromatography, gel filtration and affinity chromatography and ultracentrifugation. Methods for preparation of AAV are described in the art, e.g. U.S. Pat. Nos. 5,677,158, 6,309,634, and 6,451,306 describe examples of delivery of AAV to the central nervous system.

The AAV vector may be of any serotype selected to have specificity for a given target cell. In one embodiment the AAV vector according to the present invention is selected from the group consisting of serotypes AAV5, AAV1, AAV6, AAV7, AAV8, AAV9, AAV10, and AAV2 vectors. Further included within the scope of the application are recombinant (synthetic) AAV vectors engineered to have a particular cellular specificity and the non-human primate equivalents of AAV.

In one embodiment the vector according to the present invention is capable of infecting or transducing mammalian cells.

System for Conditionally Stabilising a Fusion Polypeptide

The present fusion polypeptides, polynucleotides, vectors and gene expression systems are useful for conditionally stabilising a fusion polypeptide. Thus are also provided herein a system for conditionally stabilising a fusion polypeptide, said system comprising a fusion polypeptide, a polynucleotide encoding a fusion polypeptide, a vector comprising such a polynucleotide or a gene expression system as described herein above, and a ligand, wherein the ligand is capable of binding to the mutant polypeptide, thereby stabilising the fusion polypeptide. In the absence of ligand, the fusion polypeptide is not stabilised, hence the polypeptide of interest is not active. The ligand is preferably a DHFR inhibitor. The fusion polypeptides used in such systems may be as described in the section "Fusion polypeptides".

Also disclosed herein is the use of such a system to conditionally stabilise a polypeptide of interest.

As can be seen in the examples (table 2), a fluorescent reporter protein fused to a Y100E DHFR mutant polypeptide has a maximal activity in the presence of ligand which is 8.93-fold higher than in the absence of ligand. The present DHFR mutant polypeptides may in some embodiments result in an increased ratio between the maximal activity of a polypeptide of interest in the presence of ligand and its maximal activity in the absence of ligand compared to what is observed for a polypeptide of interest fused to a Y100E DHFR mutant polypeptide. In some embodiments, the maximal activity of the polypeptide of interest in the presence of ligand is at least 9-fold higher than in the absence of ligand, such as at least 10-fold, such as at least 11-fold, such as at least 12-fold, such as at least 13-fold, such as at least 15-fold, such as at least 16-fold, such as at least 17-fold, such as at least 18-fold, such as at least 19-fold, such as at least 20-fold, such as at least 25-fold, such as at least 30-fold, such as at least 40-fold, such as at least 50-fold. In some embodiments, the mutant polypeptide does not differ from SEQ ID NO: 1 and SEQ ID NO: 2 only by a Y100I mutation.

The activity of the fusion polypeptide, and hence of the polypeptide of interest, is dependent on the amount of ligand. The mutant polypeptides disclosed herein have a typical dose-response curve, represented normally by a sigmoidal curve, where the inflection point corresponds to $EC_{50}$. Typically, the response will saturate after a certain amount of ligand is added to the system, which corresponds to the maximal activity the polypeptide of interest can attain in response to the ligand. The responses of the mutant polypeptides disclosed herein to a given ligand may differ: the same ligand may have a greater potency for a given mutant polypeptide than for another given mutant polypeptide, and vice versa. The greater the potency of a ligand is, the steeper the slope of the dose-response curve will be. The choice of mutant polypeptide may thus be guided by the type of response, e.g. the potency or amplitude, which it is desirable to achieve.

The activity (or stability) of the polypeptide of interest can be determined by methods known to the person of skill in the art. Such methods include enzymatic assays, spectrophotometric assays, chemiluminescent assays, calorimetric assays, binding assays, growth assays, differentiation assays. The activity of the polypeptide of interest may be determined indirectly by using a reporter polypeptide as described herein, of which the activity/stability may be determined as known in the art.

Preferably, the activity of the polypeptide of interest in the presence of ligand is such that it can exert the desired effect, e.g. a therapeutic effect, when the ligand is administered to a subject in need of such an effect.

Ligand

The present systems are based on the interaction between the mutant polypeptides and a DHFR ligand. Such a DHFR ligand may be an inhibitor of DHFR activity or it may be an enhancer of DHFR activity.

In particular embodiments, the DHFR ligand is a DHFR inhibitor selected from the group consisting of trimethoprim (trade names Proloprim, Monotrim, Triprim), brodimoprim, tetroxoprim, iclaprim (codenamed AR-100 and RO-48-2622), pyrimethamine (trade name Daraprim), proguanil (trade name Paludrine), methotrexate (formerly known as amethopterin, trade names Trexall, Rheumatrex) and pemetrexed (trade name Alimta), or analogues thereof.

The above inhibitors may be divided in two categories. Compounds of the first category are antibiotics and comprise trimethoprim (trade names Proloprim, Monotrim, Triprim), brodimoprim, tetroxoprim, iclaprim (codenamed AR-100 and RO-48-2622). These may be particularly advantageous because they are not expected to exert any activity on a mammalian host cell, and are thus "biologically silent" when administered to a mammalian subject.

Compounds of the second category comprise pyrimethamine (trade name Daraprim), proguanil (trade name Paludrine), methotrexate (formerly known as amethopterin, trade names Trexall, Rheumatrex) and pemetrexed (trade name Alimta). These are anti-cancer or anti-malarial drugs.

Accordingly, in some embodiments the system for conditionally stabilising the fusion polypeptide comprises a fusion polypeptide, a polynucleotide encoding a fusion polypeptide, a vector comprising such a polynucleotide or a gene expression system as described herein above, and a ligand capable of binding to the mutant polypeptide, wherein the ligand is a DHFR inhibitor selected from the group consisting of trimethoprim (trade names Proloprim, Monotrim, Triprim), brodimoprim, tetroxoprim, iclaprim (codenamed AR-100 and RO-48-2622), pyrimethamine (trade name Daraprim), proguanil (trade name Paludrine), methotrexate (formerly known as amethopterin, trade names Trexall, Rheumatrex) and pemetrexed (trade name Alimta). Preferably, the ligand of the system is trimethoprim, brodimoprim, tetroxoprim or iclaprim. In one embodiment the system comprises trimethoprim as ligand.

Treatment of a Disorder

Mutant polypeptides, fusion polypeptides, systems for gene expression or systems for conditionally stabilising a fusion polypeptide, and vectors comprising a polynucleotide encoding the fusion polypeptides are also provided for use in the treatment of a disease or disorder in a subject in need thereof. A method of treatment of a disease or disorder in a subject in need thereof, comprising conditionally stabilising a polypeptide of interest using the systems described herein, is also provided.

The disease or disorder may be associated with reduced or absent activity of the polypeptide of interest, or of a protein comprising the polypeptide of interest, in the subject in need of treatment. In cases where the polypeptide of interest has e.g. enzymatic activities, the disorder or disease may be associated with the lack of or with reduced levels of a product of a reaction catalysed by the polypeptide of interest.

The subject in need of treatment is any subject suffering from or suspected of suffering from a disease or disorder, for which it may be desirable to conditionally stabilise a polypeptide of interest as described herein.

In some embodiments, the treatment comprises administering a polynucleotide encoding a fusion polypeptide as described herein or a vector comprising such a polynucleotide in a subject. Such methods have been described above and are known the person of skill in the art and encompass ex vivo gene therapy, where the fusion polypeptide or vector is administered indirectly by transplanting cells capable of expressing the fusion polypeptide or comprising the vector.

The treatment further comprises administering the ligand as described above, such as a DHFR inhibitor, e.g. trimotheprim or any DHFR inhibitor described above, to the subject. The preferred mode or route of administration can be determined by the person skilled in the art and may vary depending on the nature of the disorder or disease to be treated, on the subject, on the vector used and on the ligand.

As explained herein above, the present systems are particularly advantageous in that several mutant polypeptides are provided, which may display different responsiveness to a given ligand. The present systems can thus be precisely tuned in order to match the optimal administration dosage for a given subject, depending on the nature of the subject and his/her health condition, the nature of the disorder, the nature of the ligand, and other factors as evident to the skilled person.

EXAMPLES

Plasmids

Gene synthesis and site-directed mutagenesis (Genscript) were used to generate E. coli DHFR (GenBank: J01609.1, nucleotides 558-1033) and variants, which were inserted into a plasmid with two expression cassettes. The cassettes consisted of the human CMV promoter (GenBank: KJ872540.1, nucleotides 175075-174488) driving mCherry (GenBank: HM771696.1, nucleotides 7106-7813) expression and the murine CMV promoter (GenBank: U68299.1, nucleotides 183388-182860) driving expression of respective DHFR variants fused to the N-terminus of YFP (GenBank: KJ411637.1, nucleotides 5913-6632). A set of plasmids with DHFR variants were generated, which contained GCH1 (NCBI Reference Sequence: NM_000161.2, nucleotides 162-913) instead of YFP, but were otherwise the same. The following control plasmids were used: a plasmid with only the mCherry expression cassette (pmC), a plasmid with only the YFP expression cassette (no DHFR) (pY), a plasmid with both the mCherry and YFP expression cassettes (no DHFR) (pmCY), a plasmid with the mCherry expression cassette and the human CMV promoter driving TH (NCBI Reference Sequence: NM_000360.3, nucleotides 20-1513) expression (pmC-TH) and a plasmid with the mCherry expression cassette and the human CMV promoter driving GCH1 expression (pmC-GCH). All expression cassettes included WPRE (GenBank: J04514.1, nucleotides 1093-1684) and a synthetic polyA signal sequence (Proudfoot et al 1989). Fused genes were linked by a 15 amino acid sequence coding for GGGGSGGGGSGGGGS.

Cell Culture

HEK 293 cells were grown as adherent culture using Nunclon flasks and 24-well plates (Thermo Fisher Scientific). The medium consisted of high glucose Dulbecco's modified Eagle's medium with non-essential amino acids, Phenol red, 2 mM L-glutamine and 5% fetal bovine serum (Gibco). Cells were cultured in a humidified incubator at 37° C. with 5% $CO_2$ and passaged using 0.05% trypsin with 0.48 mM EDTA (Gibco).

Cells were transfected with plasmids for DHFR variant analysis in 24-well plates using Lipofectamine 2000 (Invitrogen) according to the manufacturer's recommendations. 0.5 µg plasmid and 1.5 µl Lipofectamine 2000 were used per well. TMP was dissolved in culture medium at a concentration of 120 µM and were added to the cell culture to a concentration of 10 µM, 24 hours after transfection. Cells were harvested using trypsinization 2 days after transfections and re-suspended in DPBS with 2% fetal bovine serum and 1 mM EDTA, followed by 50 µm filtration. Draq7 (Abcam) was mixed into the cell solutions to a concentration of 0.3 µM just prior to flow cytometry analysis.

Flow Cytometry

YFP and mCherry expression of cells were quantified by flow cytometry using a BD FACS Aria III and the BD FACSDiva 6.1.3 software. YFP fluorescence was detected using a 488 nm laser and a 530/30 nm filter. mCherry fluorescence was detected using a 633 nm laser and a 660/20 nm filter. Draq7 was used to analyze viability and the fluorescence was detected using a 633 nm laser and a 730/45 nm filter. Color compensation was applied for mCherry spillover into Draq7.

Sample preparation for combined HPLC-ECD and HPLC-MS analysis of media and cells Cell pellets were analyzed for BH4 content by first adding 10 µl 100 mM HCl+5 mM ascorbic acid+50 µl 5 mM HCl+5 mM ascorbic acid to each cell pellet followed by ten 3 sec sonication runs while the samples were kept on ice. After incubation on ice for an additional 5 mins, the pellet was separated from the supernatant by centrifugation for 10 min at 14,000 rpm in 4° C. The supernatant was then transferred to 4 kDa cut off filter and spin down and stored at −80° C. until MS analysis.

Cell culture media was analyzed for DOPA after adding 5 µl 100 mM HCl+5 mM ascorbic acid to 400 µl and filtration using Amicon 3 kDa cut off spin columns after centrifugation for 1 h at 14,000 rpm in 4° C. Samples were stored at −80° C. until ECD analysis.

Variations to Residues in Loops

The following positions were identified as candidates for limited and rescuable destabilization in protein loops: R12, M42, E90, D127, W133, H141 and F153. These residues have varying numbers of interactions, such as hydrogen bonds, with other residues. They are placed so that they stabilize the surrounding structures in loops or secondary structural elements. There were two types of variations in these positions. Substitutions by alanine or glycine were made to remove the side chain interactions and replacements by other residues were intended to weaken or reverse interactions in these positions.

We found that both M42G and M42A variants are destabilizing and can be rescued by TMP. Variant M42A has higher ratio of rescue. The effect is increased when combined with substitution Y100E, however the double variant with M42G has very low activity. When the side chain of glutamate in position 90 (E90) is replaced by alanine the effect is stronger than that for aspartate. Aspartate has similar physicochemical properties as glutamate, however is shorter by one carbon atom and therefore cannot form the same contacts as the end group of the longer side chain of glutamate. The side chain of E90 interacts with amino acids from three different parts of the structure.

In the case of aspartate in position 127 (D127) the substitutions by A and N were made. The former removes the side chain, whereas in D127N the charge of carboxyl group is replaced by polar amino group. Both variants had very similar profiles to that of the reference. Combination with Y100E or Y100I did not have a major impact for the alanine variants; whereas Y100I together with the D127N had a significant destabilizing effect that could be reversed by TMP binding.

TABLE 1

DFHR protein amino acid variation sites tested are listed below. In some of the positions more than one variation was tested and listed with consecutive letters referring to each replacement for that position. Note also that some of the results presented here refer to variants with more than one amino acid substitution. Amino acid identities follow international abbreviations standards and wild type sequence refers to UniProt entry DYR_ECOLI for *Escherichia coli* (strain K12) with accession number P0ABQ4.

| Structural context | Amino acid position and variants tested | Type of variant |
|---|---|---|
| α-helix | Y100 to I or E | Cofactor binding |
| β-strand | M42 to A or G | Modification and stability of surface loops |
| | H141 to G | |
| | F153 to A, D or G | |
| Loops | R12 to Y or A | Modification and stability of surface loops |
| | N18 to T | |
| | E90 to A or D | Structural changes |
| | D122 to A | |
| | P126 to D, R or Y | |
| | D127 to A or N | |
| | W133 to A | |

Figure 2:
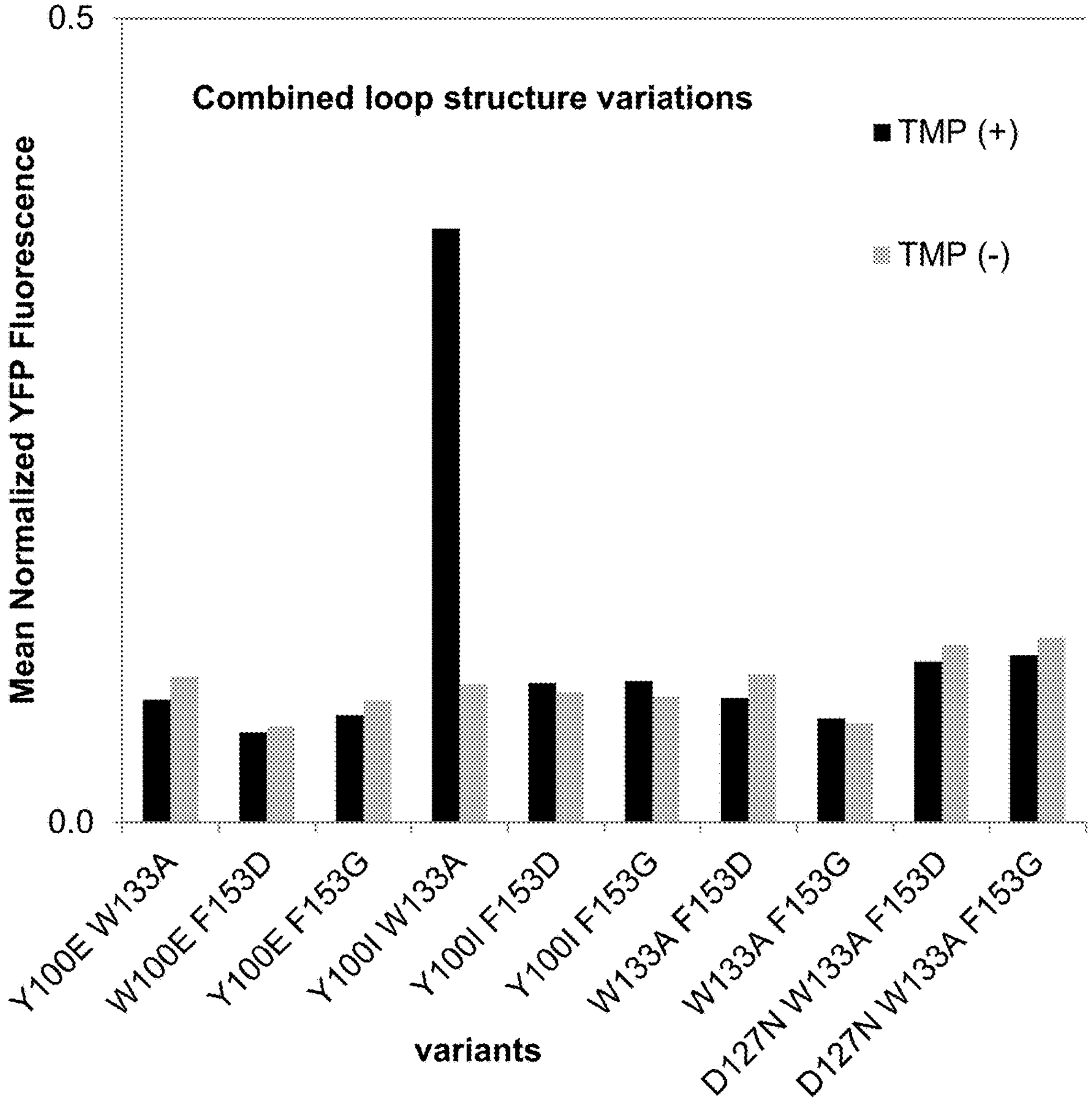
FIG. 2. Effect of loop structure variations combined with Y100I, Y100E or with other loop structure variations on the reversible destabilization of the DHFR domain fused to YFP reporter protein. Variations were studied in the presence (black bars) and absence (grey bars) of the TMP inhibitor and compared to reference construct containing the R12Y and Y100I variations (left most pair of bars). Note that the scale on the Y axis is different from the scale in FIG. 1. When W133 or F153 variants with reversible destabilization characteristics are combined with either of the Y100I or Y100E variation, the resulting combined variants are no longer rescuable with TMP. The same result was obtained when W133 and F153 variations were combined together.

Among the loop structure variations (Table 1), one of the most potent variations is tryptophan to alanine substitution in position 133 (W133A). W133 has extensive hydrogen bonding network formed both by the backbone and side chain atoms. It is buried inside the folded structure. Thus substitution of W by A at this position removes the side chain interactions. The stabilizing effect of TMP on this variant is the highest (22.9 fold) among all the variants investigated here (FIG. 1). When W133A variant is combined with other substitutions, either the destabilization is no longer reversible by binding of the inhibitor (Y100E, F153D, F153G) or the effect is significantly smaller (Y100I) (FIG. 2). Notably, removal of side chain interactions in position 141 by substitution of histidine with glycine (H141G) had an only modest destabilizing effect that did not convey sufficient magnitude of control on the TMP dependent stabilization of the protein (FIG. 1).

Phenylalanine in position 153 (F153) is located in the middle of the β-strand and forms several aromatic-aromatic side chain interactions with residues from two surrounding secondary structural elements. Substitutions of F153 by G, A or D were among the ones with strongest effect (FIG. 1). Notably, when F153D and F153G were combined with either Y100E or Y100I the constructs were no longer rescuable.

In conclusion, these results show that variations designed to affect residues binding loop structures or secondary structural elements of the protein core (namely the W133 and F153 residues) are therefore candidates for generating destabilizing domains. Substitutions which completely (by G) or almost completely (by A) remove the side chain and therefore eliminate the side chain interactions with other amino acids are among the best alterations. However, at some sites more subtle changes (e.g., F153D) present properties fulfilling the main principles of controlled stability, as well.

Combination with variants at the site detected in the previous patent (Y100) can rescue some variations that are not functional alone, however, they do not have positive impact on the strongest variants detected in here, in fact the addition of either Y100E or Y100I resulted in worse response characteristics for the respective the double variant and had reduced effect on rescue of stability by inhibitor binding (FIG. 2).

An overview of the results is shown in Table 2.

TABLE 2

List of all single site variations and their effects on YFP fluorescence is shown in the presence and absence of TMP inhibitor used as the stabilizing agent (left column). Variants that contain Y1001 modification (middle column) and those that contain Y100E variant (right column) are provided in this table.

| | Mean of Normalized YFP ratio | | Y1001 | Mean of Normalized YFP ratio | | Y100E | Mean of Normalized YFP ratio | |
|---|---|---|---|---|---|---|---|---|
| variant | (+) TMP | (−) TMP | containing variants | (+) TMP | (−) TMP | containing variants | (+) TMP | (−) TMP |
| WT | 1.513 | 1.434 | R12Y Y1001 (ref) | 1.000 | 0.107 | R12A Y100E | 0.765 | 0.033 |
| R12A | 1.384 | 1.115 | R12A Y1001 | 1.068 | 0.996 | N18T Y100E | 0.782 | 0.119 |
| N18T | 1.357 | 1.281 | N18T Y1001 | 1.650 | 0.685 | N18T Y100E D122A | 0.375 | 0.354 |
| M42A | 1.493 | 1.120 | N18T Y1001 D122A | 1.282 | 0.821 | M42A Y100E | 0.678 | 0.039 |
| M42G | 1.106 | 0.438 | Y1001 D122A | 1.428 | 1.023 | M42G Y100E | 0.049 | 0.027 |
| Y100E | 1.330 | 0.149 | Y1001 D127A | 1.447 | 1.153 | Y100E D127A | 0.966 | 0.823 |
| Y1001 | 1.226 | 1.111 | Y1001 D127N | 0.809 | 0.090 | Y100E D127N | 1.110 | 1.194 |
| D122A | 1.612 | 1.487 | Y1001 W133A | 0.369 | 0.086 | Y100E P126Y | 0.257 | 0.241 |
| P126Y | 1.499 | 0.583 | Y1001 F153D | 0.086 | 0.081 | Y100E P126D | 0.088 | 0.084 |
| P126D | 1.249 | 0.230 | Y1001 F153G | 0.088 | 0.078 | Y100E P126R | 0.273 | 0.201 |

TABLE 2-continued

List of all single site variations and their effects on YFP fluorescence is shown in the presence and absence of TMP inhibitor used as the stabilizing agent (left column). Variants that contain Y1001 modification (middle column) and those that contain Y100E variant (right column) are provided in this table.

| | Mean of Normalized YFP ratio | | Y1001 | Mean of Normalized YFP ratio | | Y100E | Mean of Normalized YFP ratio | |
|---|---|---|---|---|---|---|---|---|
| variant | (+) TMP | (−) TMP | containing variants | (+) TMP | (−) TMP | containing variants | (+) TMP | (−) TMP |
| P126R | 1.430 | 0.383 | | | | Y100E W133A | 0.076 | 0.091 |
| D127A | 1.527 | 1.479 | | | | Y100E F153D | 0.056 | 0.059 |
| D127N | 1.884 | 1.823 | | | | Y100E F153G | 0.067 | 0.076 |
| W133A | 1.196 | 0.052 | | | | | | |
| F153G | 1.089 | 0.053 | | | | | | |
| F153A | 1.108 | 0.208 | | | | | | |
| F153D | 1.189 | 0.064 | | | | | | |

Variations to Inhibitor and Cofactor Binding Residues

We found that the variants modifying cofactor binding residues at N18 or D122 did not have wanted properties. Only the variants at position Y100 could be used for stability changes as previously indicated. Both N18 and D122 have contacts with other amino acids, however not as many as Y100, which is at binding distance to numerous residues. Y100 interacts directly with NADPH and forms hydrogen bond with 15 and G96 and L104.

Replacement of N18 by threonine which is of same size but without the polar amino groups has about the same properties as the reference. Together with Y100 variants the rescue effect is evident, especially with Y100E. Y100E variation alone is similar to the R12Y Y100I reference, whereas Y100I alone showed no clear destabilization effect.

Next, the two Y100 variants were investigated together with several other substitutions (see Table 2). The strongest destabilization effect appeared for the combined Y100E M42A substitution. However, in this case, the rescue by the inhibitor was compromised.

Variations at Structural Sites

Prolines are special amino acids due to forming ring with the protein backbone. They have limited flexibility and introduce special turns to structures making the structure locally rigid. Proline 126 is in the middle of extended loop structure. Variations Y, D and R all have useful properties. When proline is substituted in this position, alterations to the backbone as well as to the interactions were expected. P126 had interaction also with Y100 and with numerous bonds with neighbouring F125. These interactions likely keep the protein tightly packed. The substitutions by D, R and Y likely affect the intramolecular bonds and render the molecule less stable. This effect can be reversed by binding TMP to the protein. Introduction of Y100E variation together with the three P126 substitutions had similar properties to the reference.

Conclusion—Rational Design of Stability Affecting Variations

The goal of this study was to substitute amino acid residues in a rational way, so that binding of the inhibitor to the structure would restore the stability, structure and function. It is essential to keep the binding site intact and therefore no major changes were made in this area. Instead, we concentrated on amino acids that have several interactions with different parts of the molecule thereby being essential for stability. These sites locate mainly on loop structures, although some of them are in secondary structural elements (β-strands) and binding surface loops to the protein core. The idea in addressing these sites is to make the structure locally more flexible and thus less stable. Inhibitor binding would help in locking the structure to the stable normal conformation. In the design a delicate balance is needed to avoid destroying the structure to such an extent that it cannot be rescued, while on the other hand significantly changing stability.

The design process was initiated by searching for amino acids outside the immediate cofactor and ligand/inhibitor binding site that have interactions, mainly hydrogen bonds but also salt bridges and aromatic-aromatic interactions, with other parts of the structure. These residues are structurally important and therefore alterations at them would reduce stability. We did not want to make major structural changes as they were considered to be too large to allow rescue. Residues with several side chain interactions with multiple parts of the molecule were prioritized.

The replacements were designed to remove side chain interactions. This is achieved by removing the side chain and replacing by glycine or alanine which do not have any carbon groups or just one in the side chain. These residues cannot form the interaction networks of the wild type side chains of larger residues. At some places also other types of substitutions were introduced, for example to replace the charged carboxyl groups of aspartate and glutamate by amino groups of asparagine or glutamine. These alterations would retain most of the side chain interactions but some interactions would either be missing or be weaker.

In conclusion, the design principles were

- to select residues having side chain interactions with other parts of the protein
- to avoid changes to the binding sites
- to remove or shorten amino acid side chains so that interactions cannot be formed
- to replace interacting groups with others that could form weaker interactions The rational design approach requires knowledge about the protein structure including structures with binding molecules (ligands, inhibitors, cofactors) based on experimental structure(s) or high quality computational model(s).

| Sequences |
|---|
| SEQ ID NO: 1 (UniProt P0ABQ4)<br>>sp\|P0ABQ4\|DYR_ECOLI Dihydrofolate reductase<br>OS = *Escherichia coli* (strain K12)<br>GN = folA PE = SV = 1<br>MISLIAALAVDRVIGMENAMPWNLPADLAWFKRNTLNKPVIMGRHTWES<br>IGRPLPGRKNIILSSQPGTDDRVTVVVKSVDEAIAACGDVPEIMVIGGG<br>RVYEQFLPKAQKLYLTHIDAEVEGDTHFPDYEPDDWESVFSEFHDADAQ<br>NSHSYCFEILERR |
| SEQ ID NO : 2<br>>ECOLI Dihydrofolate reductase R12Y G675 mutant<br>MISLIAALAVDYVIGMENAMPWNLPADLAWFKRNTLNKPVIMGRHTWES<br>IGRPLPGRKNIILSSQPSTDDRVTVVVKSVDEAIAACGDVPEIMVIGGG<br>RVYEQFLPKAQKLYLTHIDAEVEGDTHFPDYEPDDWESVFSEFHDADAQ<br>NSHSYCFEILERR |

-continued

| Sequences |
|---|
| SEQ ID NO: 3<br>>Exemplary linker<br>GGGGSGGGGSGGGGS |

REFERENCES

Bachmair, A. et al. (1986). Science 234:179-186.
Dohmen, R. J. et al. (1994) Science 263:1273-1276
Fire, A. et al. (1998) Nature 391:806-811. [0025]
Janse, D. M. et al. (2004) J. Biol. Chem. 279:21415-21420.
Kanemaki, M. et al. (2003) Nature 423:720-724.
Labib, K. et al. (2000) Science 288:1643-1646.
Medema, R. H. (2004) Biochem. J. 380:593-603.
Park, E-C. et al. (1992) Proc. Natl. Acad. Sci. U.S.A. 89:1249-1252.
Ryding, A. D. S. et al. (2001) J. Endocrinol. 171:1-14.
Schneekloth, J. S. et al. (2004) J. Am. Chem. Soc. 126:3748-3754.

The invention claimed is:

1. A fusion polypeptide comprising:

i) a mutant dihydrofolate reductase (DHFR) polypeptide comprising or consisting of an amino acid sequence having 90% or greater identical identity to the amino acid sequence of SEQ ID NO: 1 or the amino acid sequence of SEQ ID NO: 2 and comprising a mutation in at least one of the following positions: D122, P126, D127, and/or F153, and wherein the mutant DHFR polypeptide is capable of binding to a DHFR inhibitor, and ii) a polypeptide of interest, wherein the mutant DHFR polypeptide is operatively linked to the polypeptide of interest, wherein in the absence of said DHFR inhibitor, said fusion polypeptide is destabilized as compared to a DHFR polypeptide consisting of the amino acid sequence of SEQ ID NO: 1, and wherein in the presence of said DHFR inhibitor, said fusion polypeptide is stabilized.

2. The fusion polypeptide of claim 1, wherein said mutant DHFR comprises a mutation at position F153.

3. The fusion polypeptide of claim 1, wherein the mutant DHFR polypeptide comprises an amino acid sequence having 90% or greater identity to the amino acid sequence of SEQ ID NO: 1, wherein the mutation at least partly removes a side chain at the mutated position, and wherein the mutation which at least partly removes the side chain is a mutation to a glycine (G) or to an alanine (A) in at least one of the following positions P126, D127, and/or F153.

4. The fusion polypeptide of claim 1, wherein the mutant DHFR polypeptide comprises an amino acid sequence having 90% or greater identity to the amino acid sequence of SEQ ID NO: 1, wherein the mutation at least partly removes a side chain at the mutated position.

5. The fusion polypeptide of claim 1, wherein the mutant DHFR polypeptide further comprises one or more of the mutations selected from the group consisting of W133A, R12A, M42A, M42A, Y100E, R12A, Y100E, N18T, Y1001, and D127N.

6. The fusion polypeptide of claim 1, wherein the mutant DHFR polypeptide further comprises a mutation in a TMP binding pocket of the amino acid sequence of SEQ ID NO: 1.

7. The fusion polypeptide of claim 1, wherein the mutant DHFR polypeptide does not have a G67S mutation or a Y100 mutation.

8. The fusion polypeptide of claim 1, wherein the mutation is at least in positions I50 and F153, in positions R52 and F153, in positions L54 and F153, or in positions P55 and F153.

9. The fusion polypeptide of claim 1, wherein the mutant DHFR polypeptide further comprises a mutation in positions I50, R52, L54, or P55 of the amino acid sequence of SEQ ID NO: 1 or the amino acid sequence of SEQ ID NO: 2.

10. The fusion polypeptide of claim 1, wherein the mutation is F153G of the amino acid sequence of SEQ ID NO: 1 F153A of the amino acid sequence of SEQ ID NO: 1, or F153D of the amino acid sequence of SEQ ID NO: 1.

11. The fusion polypeptide of claim 1, wherein the mutation further comprises a mutation at one or more amino acid residues corresponding to M20, L28, F31, T46, S49, I50, and L54 of the amino acid sequence of SEQ ID NO: 1 or the amino acid sequence of SEQ ID NO: 2.

12. The fusion polypeptide of claim 1, wherein the mutant DHFR polypeptide is linked to the N-terminus of the polypeptide of interest, and/or wherein the mutant DHFR polypeptide is linked to the C-terminus of the polypeptide of interest.

13. The fusion polypeptide of claim 1, wherein the mutant DHFR polypeptide is further linked to a second polypeptide of interest.

14. The fusion polypeptide of claim 1, wherein the polypeptide of interest is a polypeptide selected from the group consisting of: a therapeutic polypeptide, a reporter polypeptide, an enzyme and a transcription factor.

15. The fusion polypeptide of claim 13, wherein the second polypeptide of interest is a polypeptide selected from the group consisting of: a therapeutic polypeptide, a reporter polypeptide, an enzyme and a transcription factor.

16. The fusion polypeptide of claim 1, further comprising a signal peptide capable of causing secretion of the fusion polypeptide from a mammalian cell or a nuclear localization signal capable of causing import of the fusion polypeptide in the nucleus of a cell.

17. A system for conditionally stabilizing a fusion polypeptide comprising the fusion polypeptide of claim 1 and a dihydrofolate reductase (DHFR) inhibitor, wherein the DHFR inhibitor is capable of binding to the mutant DHFR polypeptide thereby stabilizing the fusion polypeptide, wherein the maximal activity of the polypeptide of interest in the presence of the DHFR inhibitor is at least 10-fold higher than in the absence of the DHFR inhibitor.

18. The system of claim 17, wherein the fusion polypeptide further comprises a reporter gene and wherein the activity of the polypeptide of interest is determined by measuring the activity of said reporter gene.

19. The system of claim 17, wherein the DHFR inhibitor is an antibiotic.

20. The system of claim 17, wherein the DHFR inhibitor is an anti-cancer drug.

21. The fusion polypeptide of claim 1, wherein the mutant DHFR polypeptide further comprises one or more mutations selected from the group consisting of: M42 and W133.

22. The fusion polypeptide of claim 21, wherein the one or more of the mutations are selected from the group consisting of: M42A, M42G, and W133A.

* * * * *